(12) United States Patent
Wan (10) Patent No.: US 8,858,569 B2
(45) Date of Patent: Oct. 14, 2014

(54) STONE RETRIEVAL DEVICE (76) Inventor: Shaw P. Wan, Norwood, NC (US)

( * ) Notice: Subject to any disclaimer, the term of this patent is extended or adjusted under 35 U.S.C. 154(b) by 228 days.

(21) Appl. No.: 13/398,118

(22) Filed: Feb. 16, 2012

(65) Prior Publication Data

US 2013/0218144 A1 Aug. 22, 2013

(51) Int. Cl.
A61B 17/221 (2006.01)

(52) U.S. Cl.
USPC ........... 606/127; 606/113; 606/114; 606/115; 606/128; 606/2.5; 606/110; 606/130; 606/198; 604/22; 600/562; 600/104

(58) Field of Classification Search
USPC .......... 606/106, 127, 128, 113, 114, 115, 198
See application file for complete search history.

(56) References Cited

U.S. PATENT DOCUMENTS

| 1,680,490 | A |   | 8/1928 | Wappler |         |
|-----------|---|---|--------|---------|---------|
| 4,295,464 | A | * | 10/1981| Shihata | 606/127 |
| 4,899,733 | A | * | 2/1990 | DeCastro et al. | 600/104 |
| 4,927,426 | A |   | 5/1990 | Dretler |         |
| 5,147,371 | A |   | 9/1992 | Washington |     |
| 5,403,324 | A |   | 4/1995 | Ciervo  |         |
| 5,423,830 | A | * | 6/1995 | Schneebaum et al. | 606/115 |
| 5,906,621 | A | * | 5/1999 | Secrest et al. | 606/114 |
| 6,187,017 | B1|   | 2/2001 | Gregory |         |
| 6,893,451 | B2|   | 5/2005 | Cano et al. |     |
| 7,766,934 | B2| * | 8/2010 | Pal et al. | 606/200 |
| 8,246,632 | B2| * | 8/2012 | Fischer | 606/127 |
| 2003/0187457 | A1 | * | 10/2003 | Weber | 606/110 |
| 2005/0119668 | A1 | * | 6/2005 | Teague et al. | 606/127 |
| 2006/0129166 | A1 | * | 6/2006 | Lavelle | 606/113 |
| 2008/0208161 | A1 | * | 8/2008 | Kaji et al. | 604/500 |
| 2009/0198250 | A1 | * | 8/2009 | Kear | 606/127 |
| 2009/0270907 | A1 | * | 10/2009 | Todd et al. | 606/198 |
| 2009/0287193 | A1 | * | 11/2009 | Desai et al. | 606/2.5 |
| 2009/0292297 | A1 |   | 11/2009 | Ferrere |     |
| 2010/0286709 | A1 | * | 11/2010 | Diamant et al. | 606/128 |
| 2011/0004056 | A1 | * | 1/2011 | Fischer | 600/106 |
| 2011/0028987 | A1 |   | 2/2011 | Little et al. | |
| 2011/0066159 | A1 |   | 3/2011 | Teague et al. | |
| 2011/0160741 | A1 | * | 6/2011 | Asano et al. | 606/127 |
| 2011/0213381 | A1 |   | 9/2011 | Leslie et al. | |

* cited by examiner

Primary Examiner — Vy Q Bui (57) ABSTRACT

A kit for surgically removing stones comprising: a double barreled sheath including a first barrel and a second barrel joined side-by-side; a first connector which is engaged at the proximal end of the first barrel; a second connector which is engaged at the proximal end of the second barrel; a first rigid tube interconnecting the first barrel with the first connector with the first connector being releasably engaged to the first rigid tube and the first rigid tube, first barrel and first connector being co-axial; a second rigid tube interconnecting the second barrel with the second connector with the second connector being releasably engaged to the second rigid tube and the second rigid tube, second barrel and second connector being co-axial; and a wire basket retriever adapted for insertion into one of the barrels and being releasably engaged with a connector or an actuation device.

19 Claims, 10 Drawing Sheets

STONE RETRIEVAL DEVICE

FIELD OF THE INVENTION

A surgical device used to retrieve stones from a patient's body is disclosed herein below.

BACKGROUND OF THE INVENTION

Kidney stones and gallstones have plagued mankind for ages. Complications resulting from the presence of stones in the urinary tract or biliary tract often require surgical intervention to remedy the problem. A patient will require several days in the hospital to recover from a typical surgical procedure to remove a stone wherein a surgeon incises a patient's abdomen in order to remove the stone. The use of less invasive stone retrieval devises has decreased the recovery time required by a patient. Stone retrieval devices are known in the art. Prior art devices have relied upon a single sheath and a metal wire basket which is attached to a handle. The device had to be inserted into a patient under direct vision, most often through an endoscope. The device could only be deployed and retrieved for a single use after which it would have to be inserted again under direct vision through an endoscope.

While the stone retrieval devices known in the prior art performed adequately, there is significant room for improvement. The stone retrieval device disclosed below is an improvement over those known in the art.

SUMMARY OF THE INVENTION

A kit for surgically removing stones comprising: a double barreled sheath including a first barrel and a second barrel joined side-by-side, the sheath having a proximal end and a distal end; a first connector which is engaged at the proximal end of the first barrel; a second connector which is engaged at the proximal end of the second barrel; a first rigid tube interconnecting the first barrel with the first connector with the first connector being releasably engaged to the first rigid tube and the first rigid tube, first barrel and first connector being co-axial; a second rigid tube interconnecting the second barrel with the second connector with the second connector being releasably engaged to the second rigid tube and the second rigid tube, second barrel and second connector being co-axial; and a wire basket retriever adapted for insertion into one the barrel and being releasably engaged with a connector or an actuation device; where the double barreled sheath being of a size to permit passage through an endoscope.

DESCRIPTION OF THE DRAWINGS

For the purpose of illustrating the invention, there is shown in the drawings a form that is presently preferred; it being understood, however, that this invention is not limited to the precise arrangements and instrumentalities shown.

DESCRIPTION OF THE INVENTION

Figure 1:
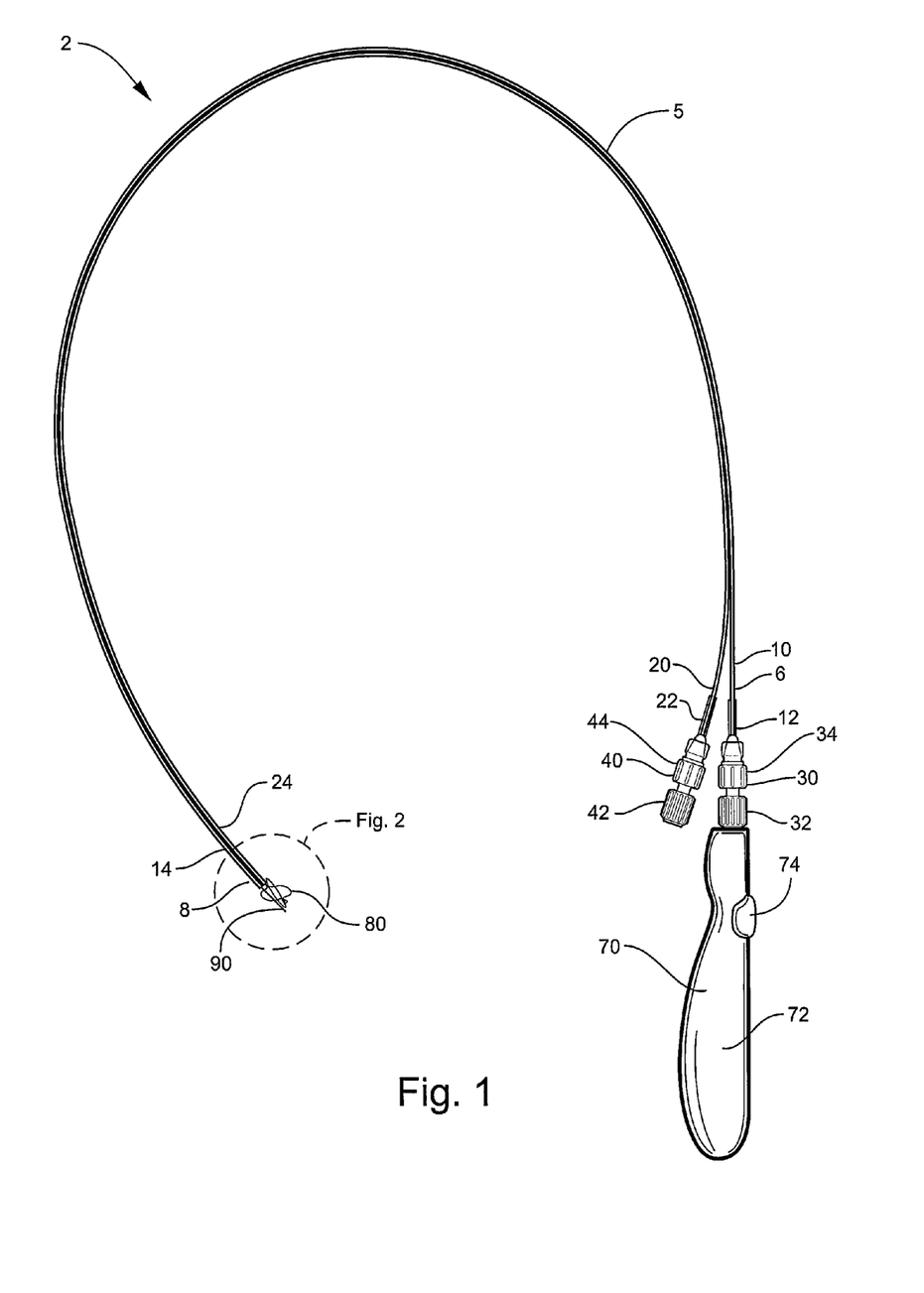
FIG. 1 is an illustration of one embodiment of the present invention.
Figures 2, 3:
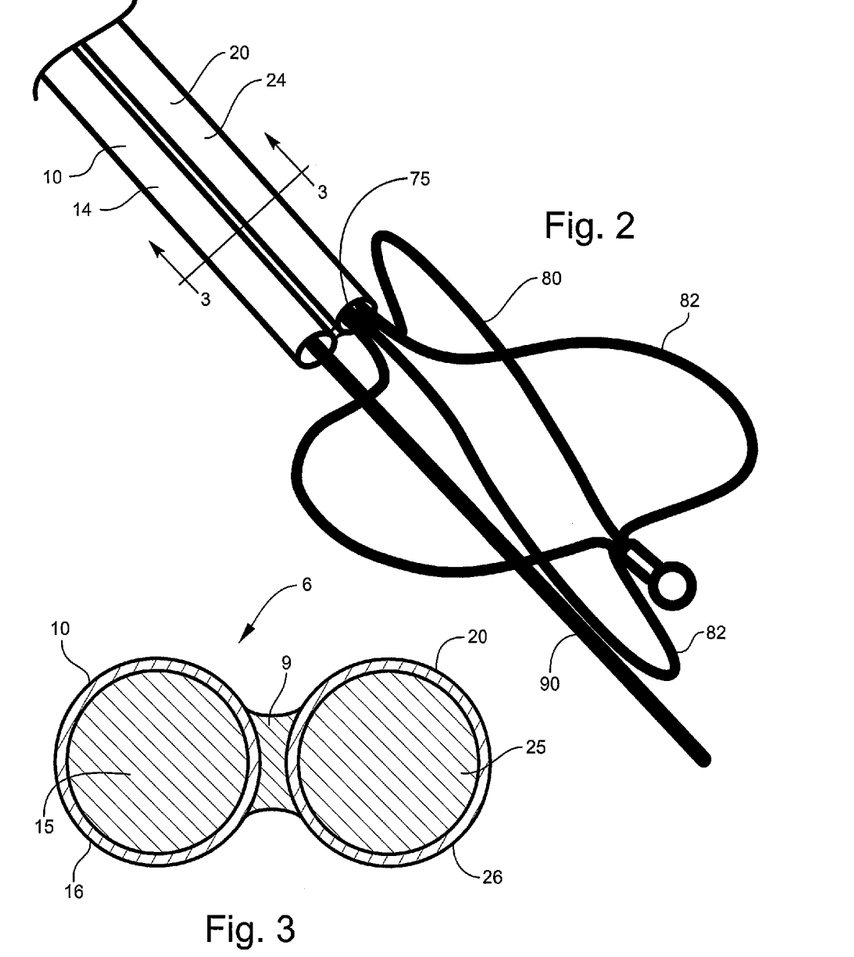
FIG. 2 is an enlarged illustration of a part of the embodiment shown in FIG. 1.
FIG. 3 is a sectional view taken along section lines 3-3 in FIG. 2.

Referring to the figures, where like numerals refer to like elements, there is shown in FIGS. 1-3 one embodiment of a kit 2 which includes a double barreled sheath 5, a pair of rigid tubes (50, 60), a pair of connectors (30, 40), an actuation device 70 and a wire basket retriever 80. Double barreled sheath 5 has a proximal end 6, a distal end 8 and includes a first barrel 10, a second barrel 20 and a bridge 9 which joins the first barrel 10 and the second barrel 20 together. The first barrel 10 has a proximal end 12, a distal end 14, a lumen 15 and an outer surface 16. The second barrel 20 has a proximal end 22, a distal end 24, a lumen 25 and an outer surface 26. In one embodiment of the present invention, the bridge 9 joins the first barrel 10 and the second barrel 20 together along the entire length of each barrel. In another embodiment, the bridge 9 runs between the first barrel 10 and the second barrel 20 from the distal ends of each barrel (14 and 24 respectively) to just short of the proximal ends of each barrel (12 and 22 respectively).

The first barrel 10 and the second barrel 20 may be made from a material selected from the group comprising: a polyether block amide (PEBA), a polyether ether ketone (PEEK), polyvinyl alcohol (PVA), Polytetrafluoroethylene (PTFE), flourinated ethylene propylene (FEP), polyvinyl, polyamide, polyimide, or polyethylene. In one embodiment, the first barrel 10 and the second barrel 20 are made from a polyether ketone. The bridge 9 may also be made from a material selected from the group comprising: a polyether block amide (PEBA), a polyether ether ketone (PEEK), polyvinyl alcohol (PVA), Polytetrafluoroethylene (PTFE), flourinated ethylene propylene (FEP), polyvinyl, polyamide, polyimide, or polyethylene. The material may be chosen so that the double barrel sheath 5 is autoclaveable. The first barrel 10, second barrel 20 and bridge 9 may all be extruded simultaneously from one of the materials above or they may each be produced individually and joined together at a later time. In one embodiment, the first barrel 10, the second barrel 20 and the bridge 9 are each made from a different material selected from the group comprising: a polyether block amide (PEBA), a polyether ether ketone (PEEK), polyvinyl alcohol (PVA), Polytetrafluoroethylene (PTFE), flourinated ethylene propylene (FEP), polyvinyl, polyamide, polyimide, or polyethylene. The length of the double barreled sheath may be in the range of 30 to 120 cm, in the range of 45 to 105 cm, in the range of 60 to 90 cm, or in the range of 70 to 80 cm. The first barrel 10 and the second barrel 20 are joined together by the bridge 9 beginning at the distal ends of the barrels (14 and 24 respectively) and continuing the entire length of each barrel until the bridge ends approximately 5 cm short of the proximal ends of the barrels (12 and 22 respectively). The length of the separation between the first barrel 10 and the second barrel 20 located at the proximal end 6 of the double barrel sheath 5 may be in the range of 2 to 8 cm, 3 to 7 cm, 4 to 6 cm, or approximately 5 cm in length.

In one embodiment, the first barrel 10 and the second barrel 20 may each have an inside diameter (lumen 15, 25 diameter) in the range of 0.05 to 0.1 cm and an outside diameter in the range of 0.06 to 0.15 cm. In another embodiment, the first barrel 10 and the second barrel 20 may each have an inside diameter in the range of 0.05 to 0.08 cm and an outside diameter in the range of 0.06 to 0.09 cm. In still another embodiment, the first barrel 10 and the second barrel 20 may each have an inside diameter in the range of 0.05 to 0.06 cm and an outside diameter in the range of 0.06 to 0.07 cm. In yet another embodiment, the first barrel 10 and the second barrel 20 may each have an inside diameter of around 0.05 cm and an outside diameter of around 0.06 cm. The double barreled sheath 5 may have an oblong shape as illustrated in FIG. 3. In various embodiments, the ratio of the length of the cross section of the double barreled sheath to the width of the cross section of the double barreled sheath may be in the range of 1.5 to 1 to 10 to 1. In various embodiments, the ratio of the length of the cross section of the double barreled sheath to the width of the cross section of the double barreled sheath may be in the range of 1.5 to 1, 2 to 1, 3 to 1, 4 to 1, 5 to 1, 6 to 1, 7 to 1, 8 to 1, 9 to 1, or 10 to 1. In one embodiment, the double barreled sheath 5 may include a radio-opaque additive to permit visualization of the double barreled sheath in an x-ray. The radio-opaque additive may be in the form of markings which delineate a utility distance such as centimeters, inches, etc. In another embodiment, the lumen 15, 25 of a barrel 10, 20 is coated with a lubricant in order to reduce the friction of cables 75 or other devices slidably disposed within the lumen 15, 25. The lubricant may be a class VI lubricant (medical, non-toxic) such as PTFE.

Figure 4:
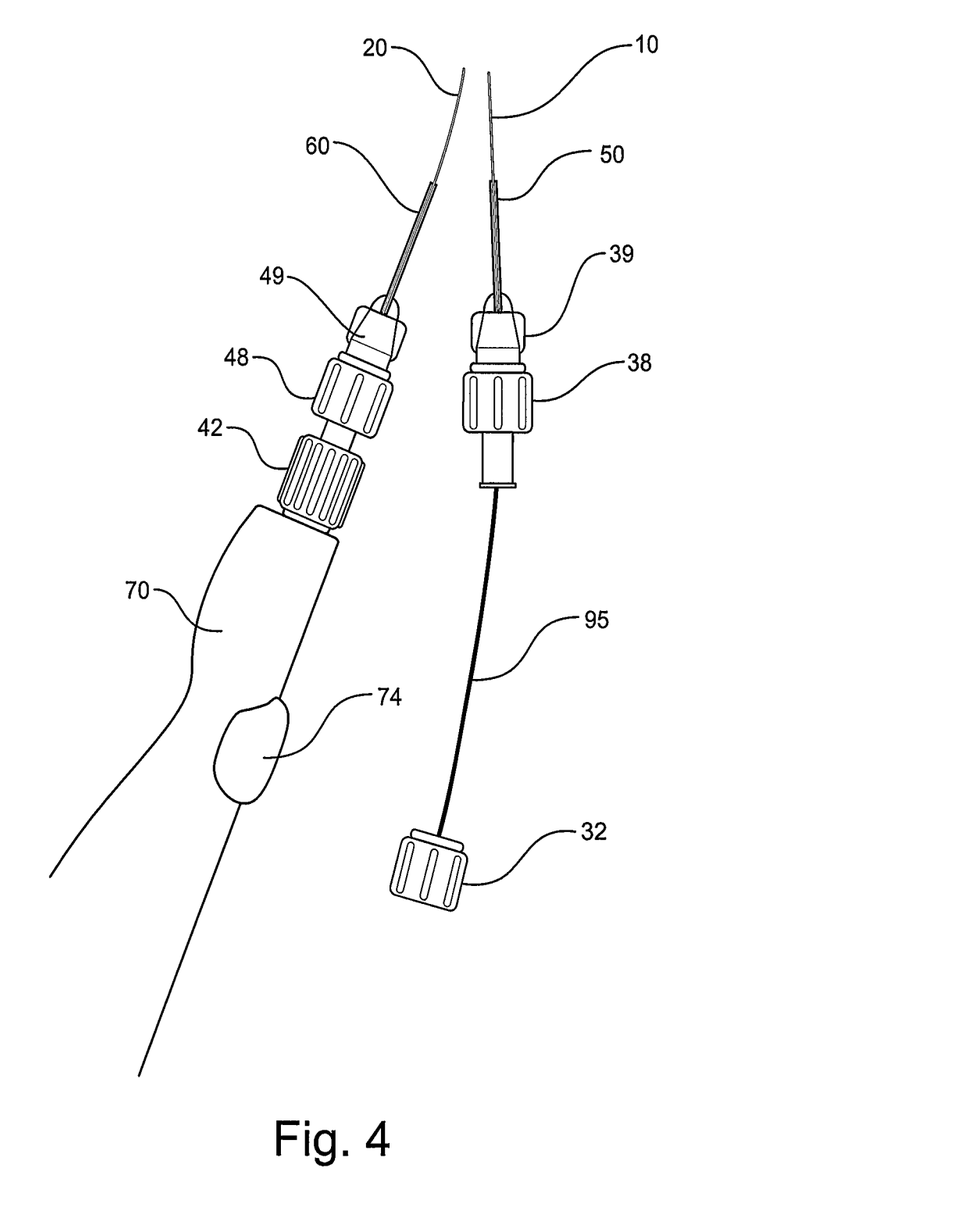
FIG. 4 is a close-up view of part of one embodiment of the present invention.
Figure 5:
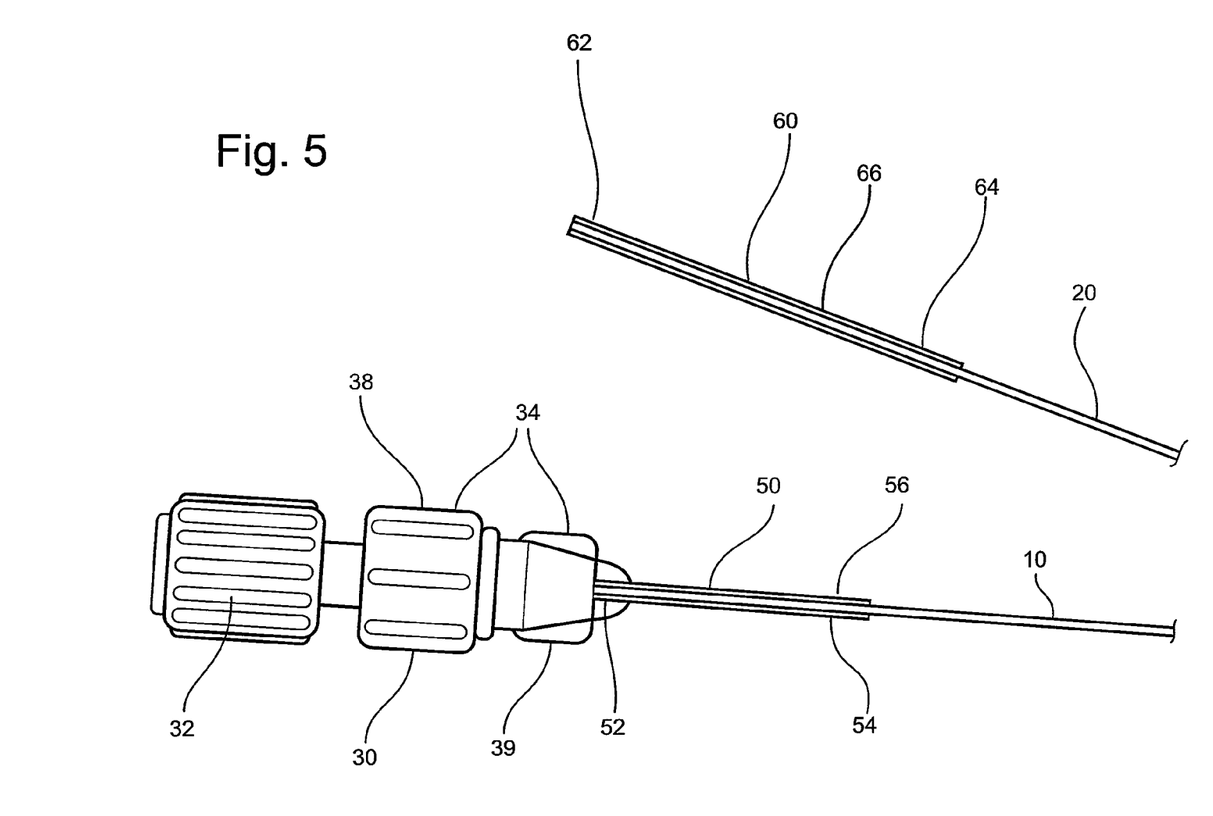
FIG. 5 is a close-up view of part of one embodiment of the present invention.

Referring now to FIGS. 1, 4 and 5, there is illustrated a first connector 30 which includes a cap 32 and an adapter 34 where the adapter 34 includes a body 38 and a tip 39. Also illustrated are a second connector 40 which includes a cap 42 and an adapter 44 where the adapter includes a body 48 and a tip 49. The first connector 30 and the second connector 40 may be made of any material, metal, plastic or combination thereof. In one embodiment, the first connector 30 and the second connector 40 may be a tuohy-borst adapter which prevents the backflow of fluid around an instrument (i.e. a wire basket retriever 80, a guide wire 90, a stylet 95, a loop 100, a grasper 105 etc.) inserted through the lumen (15, 25) of a barrel 10, 20. Operating with the tuohy-borst adapter (34 and 44) may be a male luer lock connector illustrated in FIGS. 1, 4 and 5 as a cap (32 and 42). The cap 32 of the first connector 30 is operatively associated with the adapter 34 and may be locked in place and/or unlocked by any method known in the art. The cap 42 of the second connector 40 is operatively associated with the adapter 44 and may be locked in place and/or unlocked by any method known in the art.

Connecting the first barrel 10 of the double barreled sheath 5 to the first connector 30 is the first rigid tube 50. The first rigid tube 50 includes a proximal end 52, a distal end 54, a lumen (not shown) and an outer surface 56. Connecting the second barrel 20 of the double barreled sheath 5 to the second connector 40 is the second rigid tube 60. The second rigid tube 60 includes a proximal end 62, a distal end 64, a lumen (not shown) and an outer surface 66. The first rigid tube 50 and the second rigid tube 60 may be made of any material, metal, plastic or combination thereof. In one embodiment the first rigid tube 50 and the second rigid tube 60 may be made from a material selected from the group including metal, plastic (polystyrene), or ceramic; and the first 50 and second rigid tubes 60 are more rigid than the first barrel 10 and the second barrel 20. In one embodiment of the present invention, the proximal end 12, 22 of a barrel 10, 20 passes through the lumen of a rigid tube 50, 60. In another embodiment, the proximal end 12, 22 of a barrel 10, 20 passes over the outer surface 56, 66 of a rigid tube 50, 60. In yet another embodiment, etched markings are made on the outer surface 56, 66 of each rigid tube 50, 60 to show where a connector 30, 40 may be secured to the rigid tube 50, 60. Each barrel 10, 20 may be joined to a rigid tube 50, 60 by any method or means known in the art. In one embodiment of the present invention, a barrel 10, 20 and a rigid tube 50, 60 may be extruded as a single unit. In another embodiment, a barrel 10, 20 and a rigid tube 50, 60 may be extruded as separate units. In yet another embodiment, a barrel 10, 20 and a rigid tube 50, 60 may be joined with an adhesive as in the proximal end 12, 22 of a barrel 10, 20 is adhesively joined to the distal end 54, 64, of a rigid tube 50, 60.

The cap 32 of the first connector 30 or the cap 42 of the second connector 40 may also engage an actuation device 70 as illustrated in FIGS. 1 and 4. An actuation device 70 may include a handle 72 and an actuator 74 which is engaged with a cable 75. The cable 75 then passes through the lumen of a connector 30, 40, passes through the lumen of a rigid tube 50, 60, and is then slidably disposed within the lumen of a barrel 10, 20. In one embodiment of the present invention, a wire basket retriever 80 is located on the distal end of a cable 75. The proximal end of the cable 75 is releasably engaged to an actuator 74 within the handle 72 of an actuation device 70. The actuation device may include any device known in the art. In the embodiment illustrated in FIGS. 1 and 4, an operator may hold the handle 72 and operate the actuator 74 in a slidable manner moving the actuator in a proximal and distal direction relative to the handle 72.

The kit 2 may also include additional tools and attachments which aid in the extraction of one or more stones from a patient. Each of the tools mentioned herein may be inserted into the lumen at one end of a barrel 10, 20 (i.e. the proximal end 12, 22) and fed into the lumen 15, 25 in a slideable manner until reaching the other end of the barrel (i.e. the distal end 14, 24). The tools may then be locked in place, actuated with the aid of an actuation device 70, manipulated by an individual (i.e. a physician, nurse, surgical technician, etc.), or utilized in any manner known in the art.

In one embodiment of the present invention, the kit 2 may further include a wire basket retriever 80 which is used to collect and extract stones from a patient (See FIGS. 1 and 2). The wire basket retriever 80 may be made up of two or more wires 82 which allow the wire basket to envelop an object (i.e. a stone) to either hold it in place or extract it. In one embodiment, a wire basked retriever 80 may be either permanently or temporarily attached to a cable 75 which may be either permanently or temporarily attached to a cap 32 of a first connector 30 or a cap 42 of a second connector 40 or which passes through the lumen of a connector 30, 40 to be permanently or temporarily attached to an actuator 74 of an actuation device 70.

Figure 6:
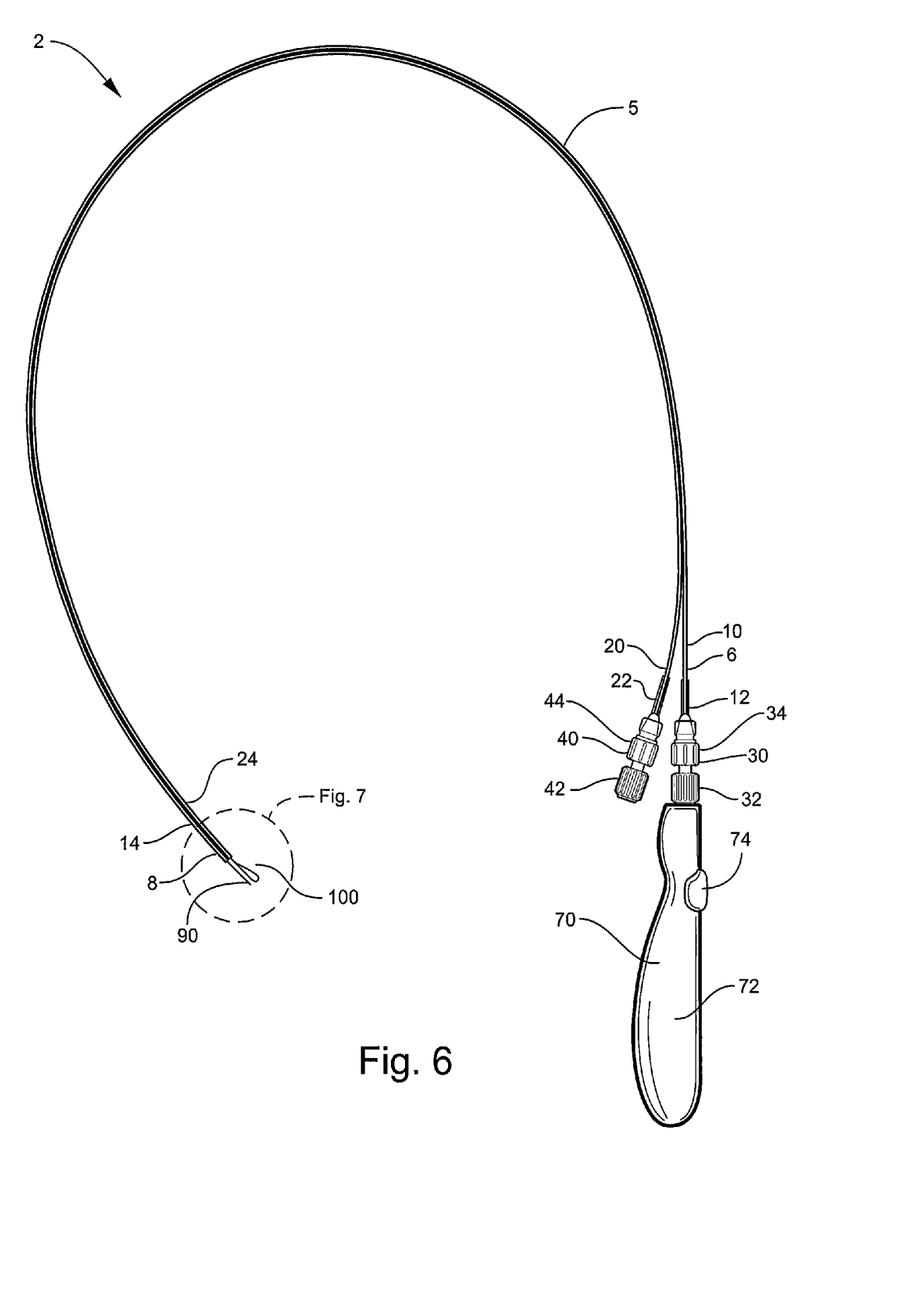
FIG. 6 is an illustration of one embodiment of the present invention.
Figure 7:
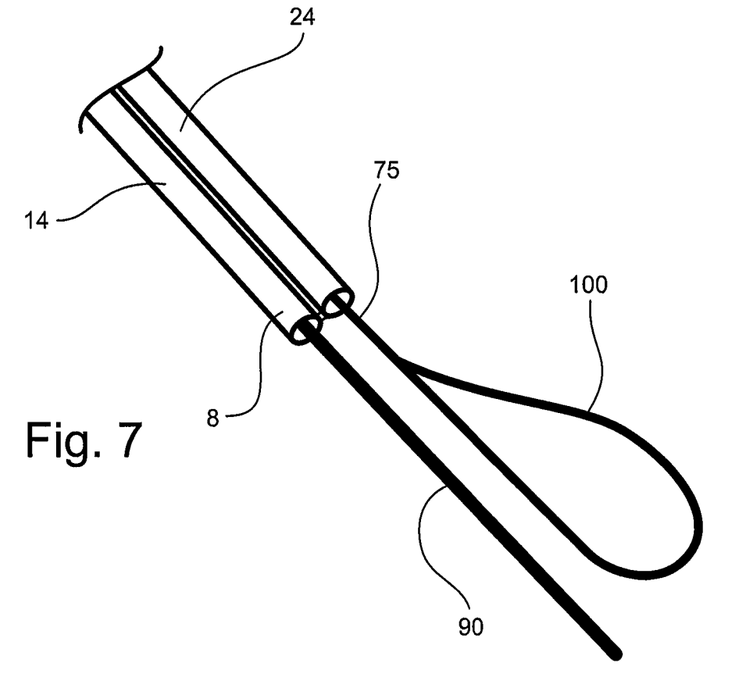
FIG. 7 is an enlarged illustration of a part of the embodiment shown in FIG. 6.

In another embodiment of the present invention, the kit 2 may further include a guide wire 90 to direct the double barreled sheath 5 to the approximate location of a stone or stones to be removed from a patient (See FIGS. 1, 2 and 6). In one embodiment, a guide wire 90 may be either permanently or temporarily attached to either a cap 32 of a first connector 30 or a cap 42 of a second connector 40 or pass through the lumen of either connector 30, 40. In another embodiment, a guide wire is not attached to any other device.

In still another embodiment, the kit 2 may further include a stylet 95 which may act to make the double barreled sheath 5 more rigid and may aid in preventing the lumen 15 of the first barrel 10 and/or the lumen 25 of the second barrel 20 from becoming obstructed or clogged. In one embodiment of the present invention, a stylet 95 may be either permanently or temporarily attached to either a cap 32 of a first connector 30 or a cap 42 of a second connector 40. In another embodiment, a stylet may be either permanently or temporarily attached to an actuation device 70 which would allow the stylet to be moved in a slideable manner within the lumen of a barrel 10, 20, the lumen of a connector 30, 40, the lumen of a rigid tube 50, 60, or any combination thereof. In yet another embodiment of the present invention, the stylet 95 may be approximately the same length as the first barrel 10 and/or the second barrel 20.

In yet another embodiment, the kit 2 may further include a loop 100 (see FIGS. 6, 7, 8 and 9) to aid in the removal of stones or other undesirable materials or tissues. The loop may be electrified to permit the cautery removal of tissues such as polyps (i.e. a polypectomy loop). A loop 100 may be either permanently or temporarily attached to a cable 75 which may be either permanently or temporarily attached to either a cap 32 of a first connector 30 or a cap 42 of a second connector 40 or which passes through the lumen of a connector 30, 40 to be permanently or temporarily attached to an actuator 74 of an actuation device 70.

Figure 10:
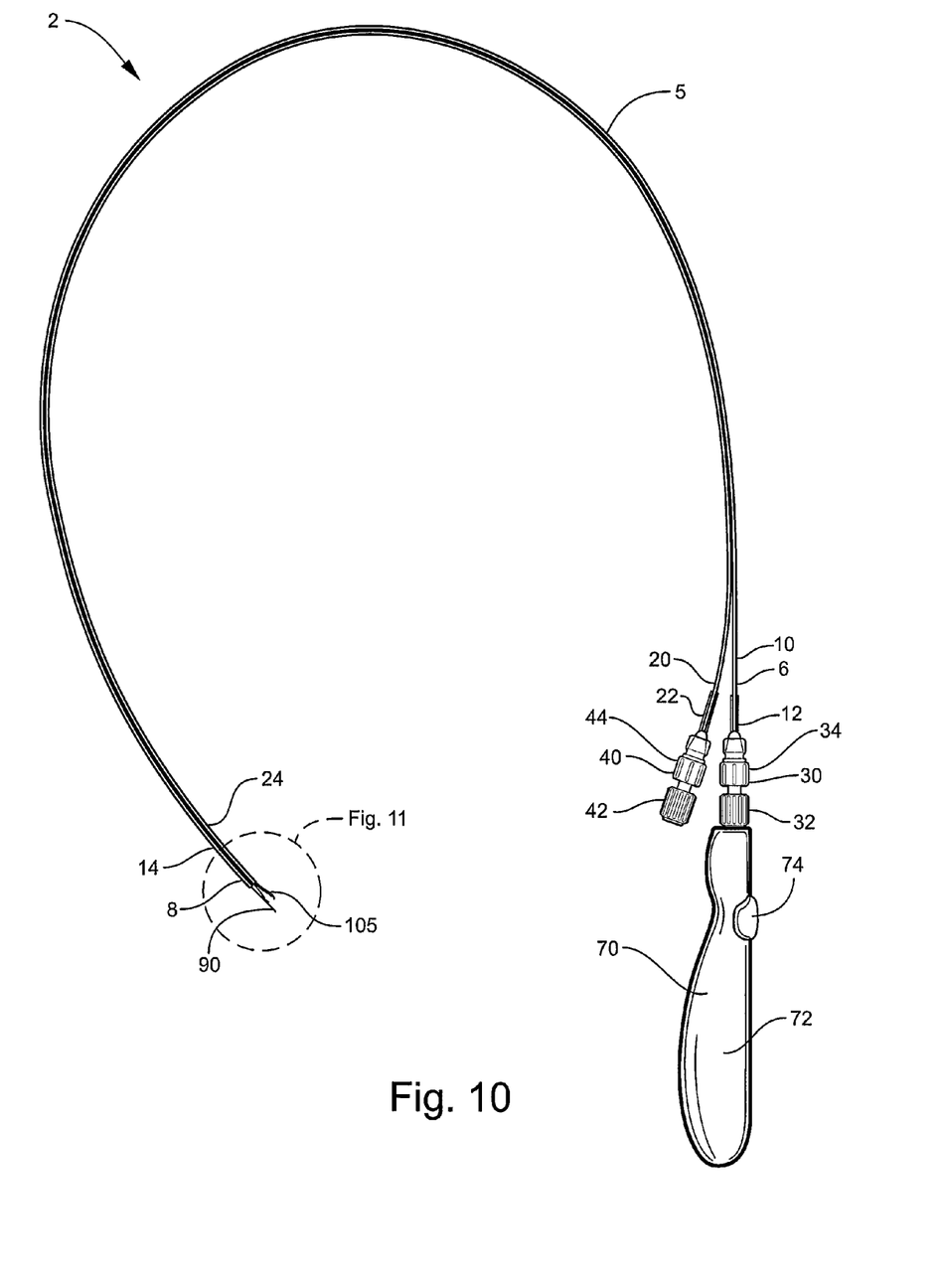
FIG. 10 is an illustration of one embodiment of the present invention.
Figure 11:
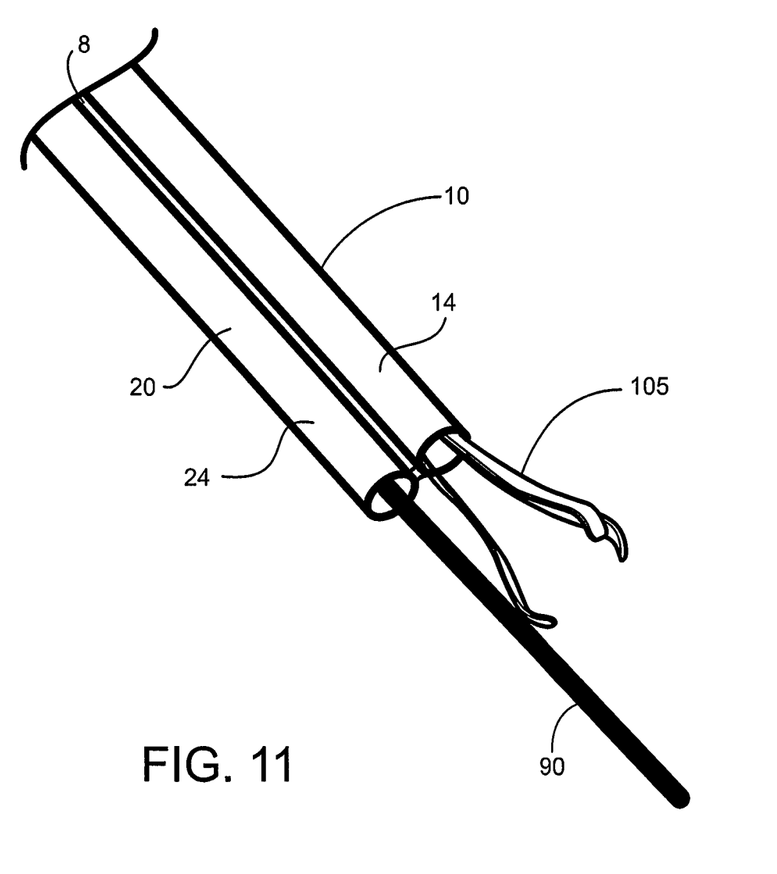
FIG. 11 is an enlarged illustration of a part of the embodiment shown in FIG. 10.

In still another embodiment, the kit 2 may further include a grasping tool 105 (see FIGS. 10 and 11) which would enable the user (i.e. a surgeon) to grasp and manipulate objects and/or tissues. In one embodiment, a grasping tool 105 may be either permanently or temporarily attached to a cable 75 which may be either permanently or temporarily attached to a cap 32 of a first connector 30 or a cap 42 of a second connector 40 or which passes through the lumen of a connector 30, 40 to be permanently or temporarily attached to an actuator 74 of an actuation device 70.

In yet another embodiment, the kit 2 may further include a laser fiber to aid in lithotripsy (the physical destruction of gallstones or kidney stones). Laser lithotripsy uses a flexible laser fiber inserted through the urethra to the stone located in the bladder, ureter or kidney. When the laser is activated, the laser beam vaporizes or breaks up the stone allowing for its collection and removal from the patient. The laser fiber may be passed through the lumen of a rigid tube 50, 60, through the lumen of a connector 30, 40 and through the lumen of a barrel 10, 20 to a close proximity of a stone or stones where it is then activated.

Figure 8:
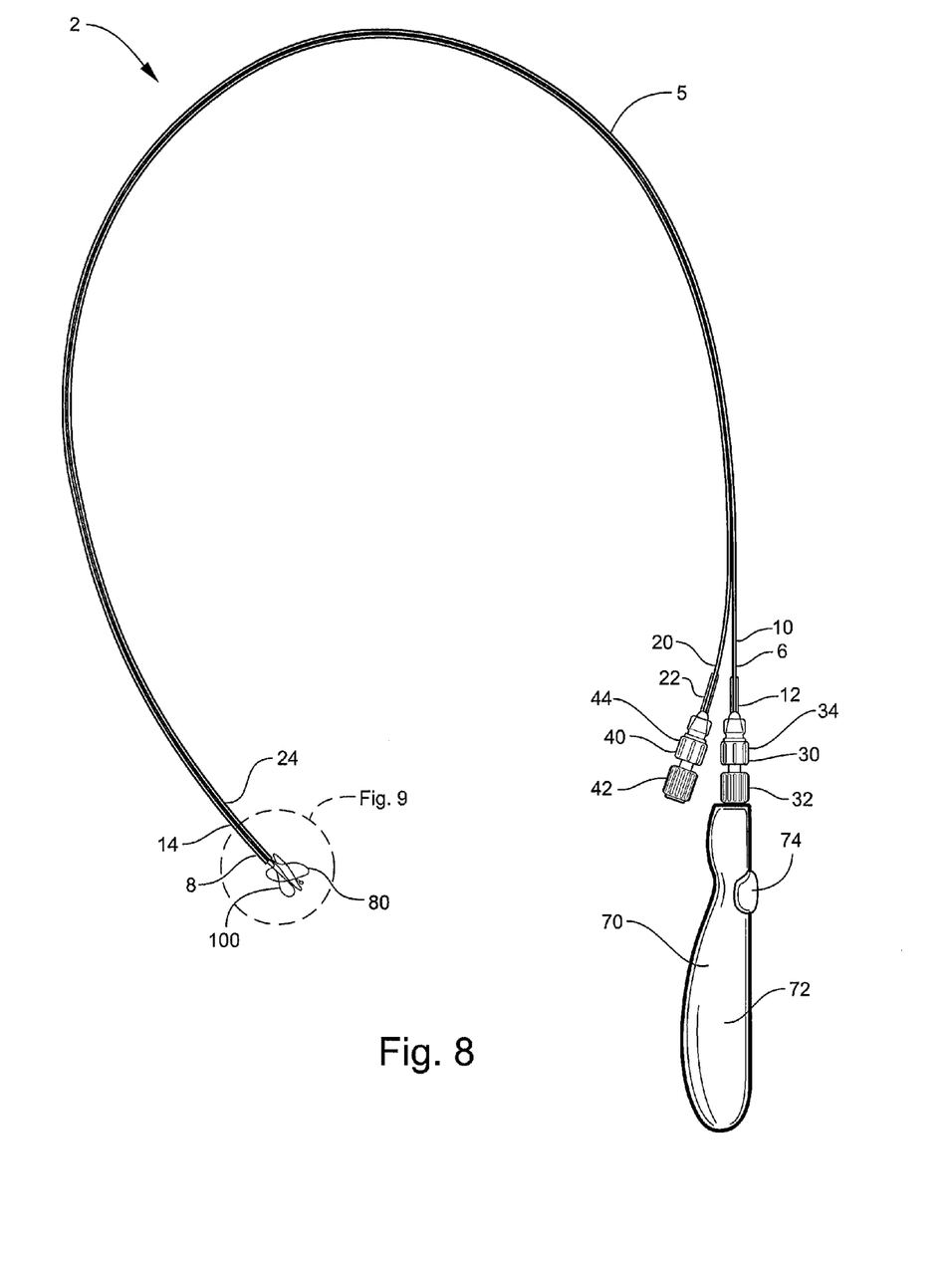
FIG. 8 is an illustration of one embodiment of the present invention.
Figure 9:
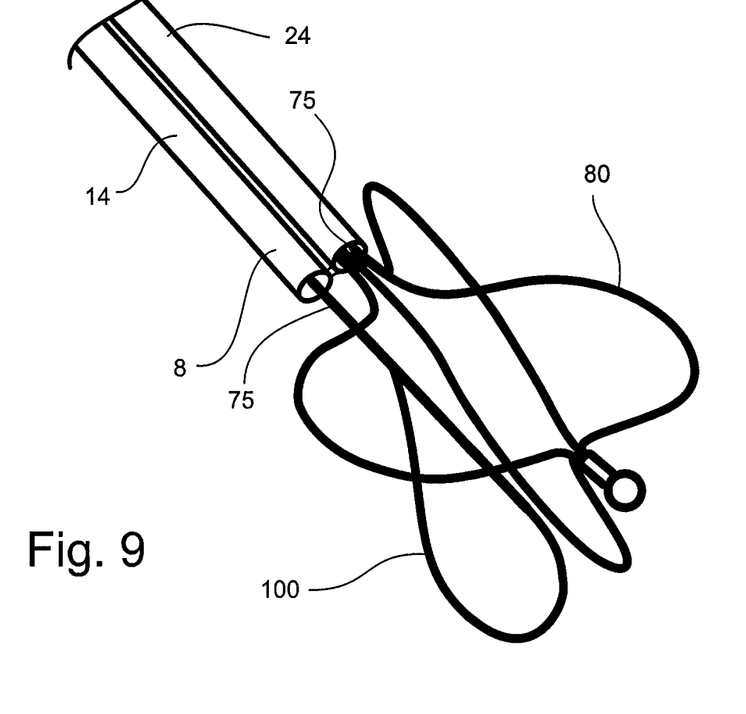
FIG. 9 is an enlarged illustration of a part of the embodiment shown in FIG. 8.

In one embodiment of the present invention, any of the additional tools and attachments described above may be used in conjunction with one another. An embodiment is illustrated in FIGS. 8 and 9 wherein both a wire basket retriever 80 and a loop 100 are used together through a single double barreled sheath 5. In another embodiment of the present invention, all parts of the kit 2 are autoclaveable.

The instant invention also includes a method for surgically removing a stone from a patient comprising the steps of: providing a kit 2 comprising: a double barreled sheath 5 including a first barrel 10 and a second barrel 20 joined side-by-side by a bridge 9 where the sheath 5 has a proximal end 6 and a distal end 8; a first connector 30 engaged at the proximal end 12 of the first barrel 10; a second connector 40 engaged at the proximal end 22 of the second barrel 20; a first rigid tube 50 interconnecting the first barrel 10 with the first connector 30 where the first connector 30 is releasably engaged to the first rigid tube 50, and the first rigid tube 50, the first barrel 10 and the first connector 30 are co-axial; a second rigid tube 60 interconnecting the second barrel 20 with the second connector 40 where the second connector 40 is releasably engaged to the second rigid tube 60, and the second rigid tube 60, second barrel 20 and second connector 40 are co-axial; and a wire basket retriever 80 adapted for insertion into one of the barrels 10, 20 and being releasably engaged with one of the connectors 30, 40 or an actuation device 70; where the double barreled sheath 5 is of a size to permit passage through an endoscope; passing a guide wire 90 into the lumen of the urinary tract or biliary tract of a patient to locate the distal end of the guide wire 90 in the proximity of the stone or stones; inserting the proximal end of the guide wire into the lumen 15 of the first barrel 10 with the wire basket retriever 80 being inside the lumen 25 of the second barrel 20; passing the double barreled sheath 5 over the guide wire 90 until the distal end of the double barreled sheath 5 reaches the distal end of the guide wire in the proximity of the stone or stones; deploying the wire basket retriever 80 from the distal end of the second barrel 20; capturing the stone; and removing the double barreled sheath 5 and the stone from the patient's lumen while leaving said guide wire 90 in place if desired.

The instant invention also includes an additional method for surgically removing a stone from a patient comprising the steps of: providing a kit 2 comprising: a double barreled sheath 5 including a first barrel 10 and a second barrel 20 joined side-by-side by a bridge 9 where the sheath 5 has a proximal end 6 and a distal end 8; a first connector 30 engaged at the proximal end 12 of the first barrel 10; a second connector 40 engaged at the proximal end 22 of the second barrel 20; a first rigid tube 50 interconnecting the first barrel 10 with the first connector 30 where the first connector 30 is releasably engaged to the first rigid tube 50, and the first rigid tube 50, the first barrel 10 and the first connector 30 are co-axial; a second rigid tube 60 interconnecting the second barrel 20 with the second connector 40 where the second connector 40 is releasably engaged to the second rigid tube 60, and the second rigid tube 60, second barrel 20 and second connector 40 are co-axial; and a grasping tool 105 adapted for insertion into one of the barrels 10, 20 and being releasably engaged with one of the connectors 30, 40 or an actuation device 70; where the double barreled sheath 5 is of a size to permit passage through an endoscope; passing a guide wire 90 into the lumen of the urinary tract or biliary tract of a patient to locate the distal end of the guide wire 90 in the proximity of the stone or stones; inserting the proximal end of the guide wire into the lumen 15 of the first barrel 10 with the wire grasping tool 105 being inside the lumen 25 of the second barrel 20; passing the double barreled sheath 5 over the guide wire 90 until the distal end of the double barreled sheath 5 reaches the distal end of the guide wire in the proximity of the stone or stones; deploying the wire basket retriever 80 from the distal end of the second barrel 20; capturing the stone; and removing the double barreled sheath 5 and the stone from the patient's lumen while leaving said guide wire 90 in place if desired.

In one embodiment of the above method(s) the first barrel 10 and the second barrel 20 may be made from a material selected from the group comprising: a polyether block amide (PEBA), a polyether ether ketone (PEEK), polyvinyl alcohol (PVA), Polytetrafluoroethylene (PTFE), flourinated ethylene propylene (FEP), polyvinyl, polyamide, polyimide, or polyethylene. In another embodiment, the first connector 30 and the second connector 40 may be made from any material, metal, plastic or combination thereof. In still another embodiment, the first rigid tube 50 and the second rigid tube 60 may be made from a material selected from the group including metal, plastic (polystyrene), or ceramic; and wherein the first 50 and second 60 rigid tubes are more rigid than the first 10 and second 20 barrel. In yet another embodiment, the double barreled sheath 5 may have an oblong shape. In still another embodiment, the above method may further include a stylet 95 to prevent the clogging of the lumen 5, 15 of the first barrel 10 and/or the second barrel 20. In yet another embodiment, the above method may further include a loop 100 which is electrified in order to permit the cautery removal of tissues such as polyps from a patient. In still another embodiment, the above method may further include a radio-opaque additive to permit visualization of the double barreled sheath 5 in an x-ray. The radio-opaque additive may be in the form of markings which delineate a utility distance such as centimeters, inches, etc. In another embodiment, the lumen 15, 25 of a barrel 10, 20 is coated with a lubricant in order to reduce the friction of cables 75 or other devices slidably disposed within the lumen 15, 25. The lubricant may be a class VI lubricant (medical, non-toxic) such as PTFE. In still another embodiment, the above method may further include the use of an endoscope during the passing of the guide wire 90 into the lumen of the urinary tract or biliary tract of a patient to locate the distal end of the guide wire 90 in the proximity of the stone or stones.

In one embodiment of the present invention, a double barreled sheath 5 may be inserted directly into the lumen of an organ through either an endoscope or through a percutaneous route. In this embodiment, the method may include inserting the double barreled sheath 5 by itself followed by the addition of a wire basket retriever 80, a stylet 95, a loop 100, a grasping tool, a laser fiber, or any combination thereof into either a first barrel 10 or a second barrel 20. The double barreled sheath 5 should be advanced to the stone or the targeted area and then confirmed through the use of a radio-opaque marker on the surface of the sheath which may be imaged in an x-ray. The method continues with the deployment of a wire basket retriever 80, generally through use of an actuator 74 on an actuation device 70, to engage and capture the stone. In the event that there are multiple stones to be extracted, a user simply removes the stylet 95 from the double barreled sheath 5 and inserts a guide wire 90 in its place. The guide wire 90 remains in place while the double barreled sheath 5, the wire basket retriever 80 and the stone are removed from the patient's body. The guide wire 90 is then used to re-insert the double barreled sheath 5 and the wire basket retriever 80 to the stone or targeted area to allow the retrieval of additional stones.

In another embodiment of the present invention, a guide wire 90 may be inserted directly into the lumen of an organ through either an endoscope or through a percutaneous route to the stone or the targeted area. In this embodiment, the method may include inserting the double barreled sheath 5 containing a wire basket retriever 80, a stylet 95, a loop 100, a grasping tool, or a laser fiber in one barrel 10, 20 while guiding the double barreled sheath 5 over the guide wire back to the stone or targeted area. The location of the double barreled sheath 5 may be confirmed through the use of a radio-opaque marker on the surface of the sheath which may be imaged in an x-ray. The method continues with the deployment of a wire basket retriever 80, generally through use of an actuator 74 on an actuation device 70, to engage and capture the stone. In the event that there are multiple stones to be extracted, a user simply removes the stylet 95 from the double barreled sheath 5 and inserts a guide wire 90 in its place. The guide wire 90 remains in place while the double barreled sheath 5, the wire basket retriever 80 and the stone are removed from the patient's body. The guide wire 90 is then used to re-insert the double barreled sheath 5 and the wire basket retriever 80 to the stone or targeted area to allow the retrieval of additional stones.

The instant invention also includes an additional method for surgically removing a stone from a patient comprising the steps of: providing a kit 2 comprising: a double barreled sheath 5 including a first barrel 10 and a second barrel 20 joined side-by-side by a bridge 9 where the sheath 5 has a proximal end 6 and a distal end 8; a first connector 30 engaged at the proximal end 12 of the first barrel 10; a second connector 40 engaged at the proximal end 22 of the second barrel 20; a first rigid tube 50 interconnecting the first barrel 10 with the first connector 30 where the first connector 30 is releasably engaged to the first rigid tube 50, and the first rigid tube 50, the first barrel 10 and the first connector 30 are co-axial; a second rigid tube 60 interconnecting the second barrel 20 with the second connector 40 where the second connector 40 is releasably engaged to the second rigid tube 60, and the second rigid tube 60, second barrel 20 and second connector 40 are co-axial; and a grasping tool 105 or a wire basket retriever 80 each being adapted for insertion into one of the barrels 10, 20 and being releasably engaged with one of the connectors 30, 40 or an actuation device 70; where the double barreled sheath 5 is of a size to permit passage through an endoscope; passing a guide wire 90 into the lumen of the urinary tract or biliary tract of a patient to locate the distal end of the guide wire 90 to a location which is distal to the proximity of the stone or stones; inserting the proximal end of the guide wire into the lumen 15 of the first barrel 10 with the grasping tool 105 or the wire basket retriever 80 being inside the lumen 25 of the second barrel 20; passing the double barreled sheath 5 over the guide wire 90 until the distal end of the double barreled sheath 5 reaches the distal end of the guide wire which is distal to the proximity of the stone(s) (the double barreled sheath 5 is then disengaged from the endoscope in the event a scope is used); deploying the grasping tool 105 or the wire basket retriever 80 from the distal end of the second barrel 20 to a location distal of the stone or stones; a scope (i.e. an endoscope, a ureteroscope, a nephroscope, a choledocoscope, or other small caliber scope) is then passed along side the double barreled sheath 5 until the scope is located in the proximal vicinity of the stone(s); a laser fiber may be deployed through the scope and activated in order to break up the stone(s) under direct visualization of the operator; capturing the stone(s) with the grasping tool 105 or the wire basket retriever 80; and removing the double barreled sheath 5 and the stone(s) from the patient's lumen while leaving said guide wire 90 in place if desired.

The oblong shape of the cross section of the double barreled sheath 5 is designed to maximize the amount of space remaining within the lumen of an anatomical tube (i.e. ureter, biliary duct, etc.) to allow the passage of a scope next to the double barreled sheath which is already in place within the lumen. Any of the above embodiments and methods may be used in conjunction with any scope known in the art including, but not limited to, an endoscope, a ureteroscope, a nephroscope, a choledocoscope, or any combination thereof.

The present invention may be embodied in other forms without departing from the spirit and the essential attributes thereof, and, accordingly, reference should be made to the appended claims, rather than to the foregoing specification, as indicating the scope of the invention.

I claim:

1. A kit for surgically removing stones comprising:
   a double barreled sheath including a first barrel and a second barrel joined side-by-side by a bridge resulting in said sheath having an oblong shape;
   said sheath, said first barrel and said second barrel each has a proximal end and a distal end;
   a first connector being releasably engaged at the proximal end of said first barrel;
   a second connector being releasably engaged at the proximal end of said second barrel;

a first rigid tube interconnecting said first barrel with said first connector;
said first connector being releasably engaged to said first rigid tube; and said first rigid tube, first barrel and first connector being co-axial;
a second rigid tube interconnecting said second barrel with said second connector;
said second connector being releasably engaged to said second rigid tube; and said second rigid tube, second barrel and second connector being co-axial; and
a wire basket retriever adapted for insertion into one of said first and second barrels and being releasably engaged with one of said first and second connectors or an actuation device;
where said double barreled sheath is of a size to permit passage through an endoscope.

2. The kit of claim 1 wherein said first barrel and said second barrel are made from a material selected from the group comprising: a polyether block amide (PEBA), a polyether ether ketone (PEEK), polyvinyl alcohol (PVA), Polytetrafluoroethylene (PTFE), flourinated ethylene propylene (FEP), polyvinyl, polyamide, polyimide, or polyethylene.

3. The kit of claim 1 wherein said first connector and said second connector are made from any material including metal, plastic or combination thereof.

4. The kit of claim 1 wherein said first rigid tube and said second rigid tube are made from a material selected from the group including metal, plastic (including polystyrene), or ceramic; and wherein said first and second rigid tubes are more rigid than said first and second barrel.

5. The kit of claim 1 further including a guide wire to direct said double barreled sheath to a location of a stone or stones to be removed.

6. The kit of claim 1 further including a stylet to prevent clogging of the lumen of said first barrel and/or said second barrel.

7. The kit of claim 1 further including a loop to permit cautery removal of tissues.

8. The kit of claim 1 further including a radio-opaque additive to permit visualization of the double barreled sheath in an x-ray.

9. The kit of claim 1 further including a grasping tool to aid in removal of foreign materials or tissues from a patient.

10. A method for surgically removing a stone comprising the steps of:
providing a kit comprising:
a double barreled sheath including a first barrel and a second barrel joined side-by-side by a bridge resulting in said sheath having an oblong shape;
said sheath, said first barrel and said second barrel each has a proximal end and a distal end;
a first connector being releasably engaged at the proximal end of said first barrel;
a second connector being releasably engaged at the proximal end of said second barrel;
a first rigid tube interconnecting said first barrel with said first connector;
said first connector being releasably engaged to said first rigid tube; and said first rigid tube, first barrel and first connector being co-axial;
a second rigid tube interconnecting said second barrel with said second connector;
said second connector being releasably engaged to said second rigid tube; and said second rigid tube, second barrel and second connector being co-axial; and
a wire basket retriever adapted for insertion into one of said first and second barrels and being releasably engaged with one of said first and second connectors or an actuation device;
where said double barreled sheath is of a size to permit passage through an endoscope;
passing a guide wire into a lumen of a urinary tract or biliary tract of a patient to locate the distal end of the guide wire in the proximity of said stone;
inserting the proximal end of said guide wire into the lumen of said first barrel with said wire basket retriever being inside the lumen of said second barrel;
passing said double barreled sheath over said guide wire until the distal end of the double barreled sheath reaches the distal end of said guide wire in the proximity of said stone or stones;
deploying said wire basket retriever from the distal end of said second barrel;
capturing said stone with said wire basket retriever; and
removing said double barreled sheath and said stone from the lumen of the urinary tract or biliary tract of the patient while leaving said guide wire in place if desired.

11. The method of claim 10 wherein said first barrel and said second barrel are made from a material selected from the group comprising: a polyether block amide (PEBA), a polyether ether ketone (PEEK), polyvinyl alcohol (PVA), Polytetrafluoroethylene (PTFE), flourinated ethylene propylene (FEP), polyvinyl, polyamide, polyimide, or polyethylene.

12. The method of claim 10 wherein said first connector and said second connector are made from any material, metal, plastic or combination thereof; and
wherein said first rigid tube and said second rigid tube are made from a material selected from the group including metal, plastic (including polystyrene), or ceramic; and wherein said first and second rigid tubes are more rigid than said first and second barrel.

13. The method of claim 10 wherein said double barreled sheath has an oblong shape.

14. The method of claim 10 further including a stylet to prevent the clogging of the lumen of said first barrel and/or said second barrel.

15. The method of claim 10 further including a loop to permit cautery removal of tissues.

16. The method of claim 10 further including a radio-opaque additive to permit visualization of the double barreled sheath in an x-ray.

17. The method of claim 10 further including use of an endoscope during the passing of said guide wire into the lumen of the urinary tract or biliary tract of the patient to locate the distal end of the guide wire in the proximity of said stone or stones.

18. The method of claim 10 further including the steps of:
passing a guide wire into the lumen of the urinary tract or biliary tract of a patient to locate the distal end of the guide wire to a location which is distal to the proximity of said stone or stones;
inserting the proximal end of the guide wire into the lumen of said first barrel with said wire basket retriever being inside the lumen of said second barrel;
passing said double barreled sheath over the guide wire until the distal end of said double barreled sheath reaches the distal end of the guide wire which is distal to the proximity of the stone(s);
deploying said wire basket retriever from the distal end of said second barrel to a location distal of said stone or stones;

passing a scope along side said double barreled sheath until said scope is located in the proximal vicinity of said stone(s);

deploying a laser fiber through said scope;

activating said laser fiber in order to break up the stone(s);

capturing said stone(s); and removing the double barreled sheath and said stone(s) from the patient's lumen while leaving said guide wire in place if desired.

19. A method for surgically removing a stone comprising the steps of:

providing a kit comprising:

a double barreled sheath including a first barrel and a second barrel joined side-by-side by a bridge resulting in said sheath having an oblong shape;

said sheath, said first barrel and said second barrel each has having a proximal end and a distal end;

a first connector being releasably engaged at the proximal end of said first barrel;

a second connector being releasably engaged at the proximal end of said second barrel;

a first rigid tube interconnecting said first barrel with said first connector;

said first connector being releasably engaged to said first rigid tube; and said first rigid tube, first barrel and first connector being co-axial;

a second rigid tube interconnecting said second barrel with said second connector;

said second connector being releasably engaged to said second rigid tube; and said second rigid tube, second barrel and second connector being co-axial; and a grasping tool adapted for insertion into one of said first and second barrels and being releasably engaged with one of said first and second connectors or an actuation device;

where said double barreled sheath is of a size to permit passage through an endoscope;

passing a guide wire into a lumen of a urinary tract or biliary tract of a patient to locate the distal end of the guide wire in the proximity of said stone;

inserting the proximal end of said guide wire into the lumen of said first barrel with a wire basket retriever being inside a lumen of said second barrel;

passing said double barreled sheath over said guide wire until the distal end of the double barreled sheath reaches the distal end of said guide wire in the proximity of said stone or stones;

deploying said grasping tool from the distal end of said second barrel;

capturing said stone or stones with said grasping tool; and removing said double barreled sheath and said stone from the lumen of the urinary tract or biliary tract of the patient while leaving said guide wire in place if desired.

* * * * *